US007714090B2

(12) United States Patent
Iwamoto et al.

(10) Patent No.: US 7,714,090 B2
(45) Date of Patent: May 11, 2010

(54) (METH)ACRYLATE COMPOUND AND PROCESS FOR THE PRODUCTION THEREOF, (METH)ACRYLATE COPOLYMER AND PROCESS FOR THE PRODUCTION OF (METH)ACRYLATE COPOLYMER, AND SOFT INTRAOCULAR LENS

(75) Inventors: Hidetoshi Iwamoto, Fukaya (JP); Yoko Katsuki, Shinjuku-ku (JP)

(73) Assignee: Hoya Corporation, Tokyo (JP)

( * ) Notice: Subject to any disclaimer, the term of this patent is extended or adjusted under 35 U.S.C. 154(b) by 331 days.

(21) Appl. No.: 11/885,440

(22) PCT Filed: Mar. 1, 2006

(86) PCT No.: PCT/JP2006/304424

§ 371 (c)(1),
(2), (4) Date: Oct. 10, 2007

(87) PCT Pub. No.: WO2006/095750

PCT Pub. Date: Sep. 14, 2006

(65) Prior Publication Data

US 2008/0139769 A1 Jun. 12, 2008

(30) Foreign Application Priority Data

Mar. 9, 2005 (JP) ............................. 2005-065837

(51) Int. Cl.
C08F 20/26 (2006.01)
C08F 26/06 (2006.01)
A61F 2/16 (2006.01)

(52) U.S. Cl. .................... 526/320; 526/259; 526/307.4; 526/328.5; 623/6.11; 623/6.6

(58) Field of Classification Search ................. 526/259, 526/307.4, 320, 328.5; 623/6.11, 6.6
See application file for complete search history.

(56) References Cited

U.S. PATENT DOCUMENTS 6,326,448 B1 12/2001 Ojio et al.

6,335,409 B1 1/2002 Herr et al.

FOREIGN PATENT DOCUMENTS

| CA | 2055138 | 9/1998 |
|---|---|---|
| JP | 58-128393 | 7/1983 |
| JP | 4-292609 | 10/1992 |
| JP | 06-088064 | 3/1994 |
| JP | 06-199961 | 7/1994 |
| JP | 8-503506 | 4/1996 |
| JP | 08-120149 | 5/1996 |
| JP | 8-173522 | 7/1996 |
| JP | 08-173522 | 7/1996 |
| JP | 8-224295 | 9/1996 |
| JP | 11-56998 | 3/1999 |
| JP | 11-102071 | 4/1999 |
| JP | 11-326848 | 11/1999 |
| JP | 2001-316426 | 11/2001 |
| WO | WO 94/11764 | 5/1994 |
| WO | WO 96/40303 | 12/1996 |
| WO | WO 99/52570 | 10/1999 |

OTHER PUBLICATIONS

International Search Report for PCT/JP2006/304424 mailed May 16, 2006 (English and Japanese).
Written Opinion for PCT/JP2006/304424 mailed May 16, 2006 (3 pages).

*Primary Examiner*—Helen L. Pezzuto
(74) *Attorney, Agent, or Firm*—Nixon & Vanderhye P.C.

(57) ABSTRACT

A (meth)acrylate copolymer obtained by copolymerization of a monomer mixture containing a monomer (A) of the general formula (I),

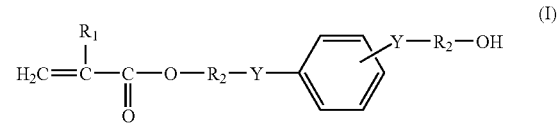

wherein $R_1$ is a hydrogen atom or methyl, $R_2$ is a linear or branched alkylene group having 1 to 8 carbon atoms and Y is a single bond or an oxygen atom, a monomer (B) copolymerizable with the monomer (A) and a crosslinking monomer (C).

9 Claims, No Drawings

(METH)ACRYLATE COMPOUND AND PROCESS FOR THE PRODUCTION THEREOF, (METH)ACRYLATE COPOLYMER AND PROCESS FOR THE PRODUCTION OF (METH)ACRYLATE COPOLYMER, AND SOFT INTRAOCULAR LENS

This application is the U.S. national phase of International Application No. PCT/JP2006/304424 filed 1 Mar. 2006, which designated the U.S. and claims priority to JP 2005-065837 filed 9 Mar. 2005, the entire contents of each of which are hereby incorporated by reference.

TECHNICAL FIELD

The present invention relates to a (meth)acrylate compound and a process for the production thereof, a (meth)acrylate copolymer and a process for the production of a (meth)acrylate copolymer, and a soft intraocular lens.

TECHNICAL BACKGROUND

With an increase in the population of aged people, the number of aged patients having senile cataract has noticeably increased. For treating a patient with cataract, the opaque lens and cortex are removed and the vision is corrected with an ophthalmic lens or a contact lens, or an intraocular lens is inserted. It is a generally practiced method at present to remove the entire lens and then fix an intraocular lens in the capsule.

In recent years, as ultrasonic emulsification suction has come to be widely used, an intraocular lens that is insertable through a small incision has been developed and widely clinically used for reducing post-surgery astigmatism and surgery invasion. This lens is a soft intraocular lens that can be inserted through a small incision since its optic portion is formed of a soft material and is hence foldable.

Various inventions have been so far made for materials for intraocular lenses excellent in transparency and flexibility. For example, there have been proposed an intraocular lens obtained by copolymerization of a mixture containing at least two (meth)acrylate monomers having aromatic rings and a crosslinking monomer (see JP-A-4-292609), an intraocular lens obtained by copolymerization of a mixture containing a perfluorooctylethyloxypropylene (meth)acrylate monomer, a 2-phenylethyl(meth)acrylate monomer, an alkyl(meth)acrylate monomer and a crosslinking monomer (see JP-A-8-224295), an intraocular lens formed of a copolymer from a monomer of which a homopolymer has a refractive index of 1.5 or more, a monomer of which a homopolymer has a glass transition temperature of less than 30° C. and a crosslinking monomer, and the like (see Japanese Translation Version No. 8-503506 of PCT Application).

All of these intraocular lenses have transparency and flexibility and are deformable, so that they can be inserted through a relatively small incision. After such an intraocular lens is implanted in the eye, however, a so-called glistening phenomenon takes place, in which the transparency of the intraocular lens is greatly decreased or removed due to numerous small and large water bubbles that are thought to be caused by a phase separation of water that has infiltrated into a lens material, from the lens material.

For overcoming the above glistening problem, there have been proposed a copolymer formed from only one main aryl acrylic hydrophobic monomer and one main hydrophilic monomer present in an amount that is not larger than the amount of the former (see JP-A-2001-316426) and a soft intraocular lens that is formed of a polymer obtained by polymerization of a monomer component containing a hydrophilic monomer and that has a water absorptivity of 1.5 to 4.5% by weight (see JP-A-11-56998).

It can be thought that these materials can inhibit the phenomenon of glistening, etc., which occurs after the implantation of an intraocular lens in the eye. Since, however, a hydrophilic monomer is contained, the refractive index is decreased. Further, when a hydrophilic monomer such as 2-hydroxyethyl methacrylate ("HEMA" hereinafter) is used, the phenomenon of calcium deposition takes place, which may possibly cause the opacification of a lens. Further, when a hydrophilic monomer such as N-vinylpyrrolidone is used, the polymerization reactivity may be decreased and an unreacted monomer may be eluted.

Further, there is proposed an intraocular lens material that is a copolymer obtained by polymerization of a monomer mixture containing 2-hydroxy-3-phenoxypropyl acrylate as a monomer component and a crosslinking agent (JP-A-8-173522).

The copolymer described in JP-A-8-173522 exhibits low tackiness (low adhesion), a low water content and high refractivity. However, the present inventors have ascertained that this copolymer is insufficient for inhibiting the glistening phenomenon although it contains, as a structural unit of the copolymer, a unit derived from a hydroxyl-group-containing monomer such as 2-hydroxy-3-phenoxypropyl acrylate (see Comparative Example to be described later).

DISCLOSURE OF THE INVENTION

The present invention has been made for overcoming the above problems, and it is an object of the present invention to provide a novel (meth)acrylate compound and a process for the production thereof, a (meth)acrylate copolymer having a unit derived from the above (meth)acrylate compound, having high refractivity and having both flexibility with which a lens formed therefrom is foldable and transparency capable of preventing (free of) the occurrence of the glistening, a process for the production of the above (meth)acrylate copolymer and a soft intraocular lens comprising the above (meth)acrylate copolymer.

For achieving the above object, the present inventors have made diligent studies and as a result have found a novel (meth)acrylate compound. Further they have found that the above object can be achieved by a (meth)acrylate copolymer having a unit derived from the above (meth)acrylate compound. The present invention has been accordingly completed.

That is, the present invention provides;

(1) a (meth)acrylate compound of the general formula (I),

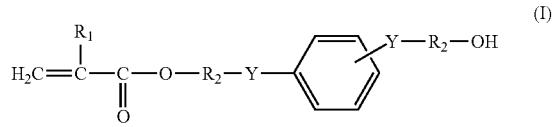

wherein $R_1$ is a hydrogen atom or methyl, $R_2$ is a linear or branched alkylene group having 1 to 8 carbon atoms and Y is a single bond or an oxygen atom, (2) a process for the production of a (meth)acrylate compound recited in the above (1), which comprises reacting a compound of the general formula (II),

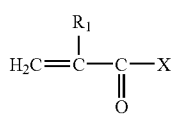

wherein $R_1$ is a hydrogen atom or methyl and X is a halogen atom, with a compound of the general formula (III),

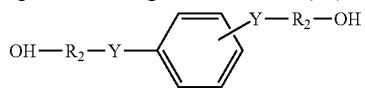

wherein $R_2$ is a linear or branched alkylene group having 1 to 8 carbon atoms and Y is a single bond or an oxygen atom, (3) a (meth)acrylate copolymer obtained by copolymerization of a monomer mixture containing a methacrylate monomer (A) of the general formula (I),

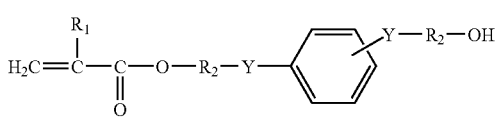

wherein $R_1$ is a hydrogen atom or methyl, $R_2$ is a linear or branched alkylene group having 1 to 8 carbon atoms and Y is a single bond or an oxygen atom, a monomer (B) copolymerizable with the (meth)acrylate monomer (A) and a crosslinking monomer (C), (4) a (meth)acrylate copolymer as recited in the above (3), wherein a unit derived from the monomer (A) and a unit derived from the monomer (B) have a mass ratio (a mass of the unit derived from the monomer (A)/a mass of the unit derived from the monomer (B)) of 1/99 to 40/60, (5) a (meth)acrylate copolymer as recited in the above (3) or (4), wherein the monomer (B) is selected from a monomer ($B_1$) of the general formula (IV),

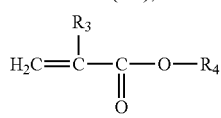

wherein $R_3$ is a hydrogen atom or methyl and $R_4$ is a linear or branched alkyl group having 3 to 12 carbon atoms, or a monomer ($B_2$) of the general formula (V),

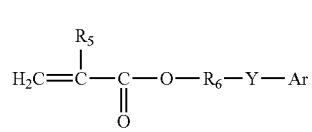

wherein $R_5$ is a hydrogen atom or methyl, $R_6$ is a single bond or a linear or branched alkylene group having 1 to 8 carbon atoms, Y is a single bond or an oxygen atom and Ar is a substituted or non-substituted phenyl group or 4-(α,α-dimethylbenzyl)phenyl, (6) a (meth)acrylate copolymer as recited in any one of the above (3) to (5), which contains a unit derived from a monomer having capability of absorbing ultraviolet ray.

(7) a (meth)acrylate copolymer as recited in the above (6), which contains 0.05 to 3 mass %, based on the total amount of a unit derived from the monomer (A) and a unit from the monomer (B), of a unit derived from the monomer having capability of absorbing ultraviolet ray, (8) a (meth)acrylate copolymer as recited in the above (6) or (7), wherein the monomer having capability of absorbing ultraviolet is a compound of the formula (VI),

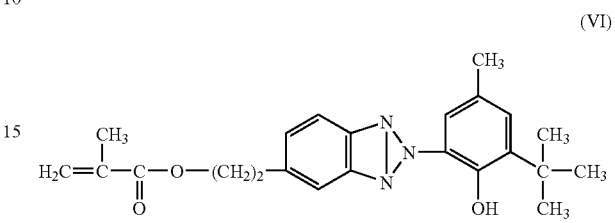

(9) a (meth)acrylate copolymer as recited in any one of the above (3) to (8), which contains a unit derived from a monomer having capability of coloring the (meth)acrylate copolymer in yellow,

(10) a (meth)acrylate copolymer as recited in the above (9), which contains 0.005 to 0.5 mass %, based on the total amount of a unit derived from the monomer (A) and a unit from the monomer (B), of the unit derived from a monomer having capability of coloring the (meth)acrylate copolymer in yellow,

(11) A (meth)acrylate copolymer as recited in the above (9) or (10), wherein the monomer having capability of coloring the (meth)acrylate copolymer in yellow is a compound of the formula (VII),

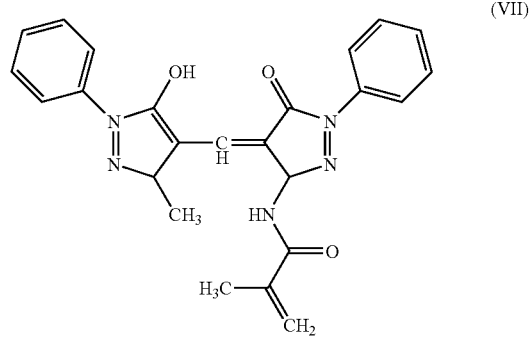

(12) a process for the production of a (meth)acrylate copolymer, which comprises copolymerizing a monomer mixture containing a monomer (A) of the general formula (I),

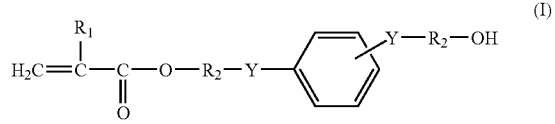

wherein $R_1$ is a hydrogen atom or methyl, $R_2$ is a linear or branched alkylene group having 1 to 8 carbon atoms and Y is a single bond or an oxygen atom, a monomer (B) copolymerizable with the monomer (A) and a crosslinking monomer (C), in the presence of a polymerization catalyst and/or under a condition where light is applied, and

(13) a soft intraocular lens comprising a (meth)acrylate copolymer recited in any one of the above (3) to (11).

According to the present invention, there can be provided a novel (meth)acrylate compound and a process for the production thereof, a (meth)acrylate copolymer having a unit derived from the above (meth)acrylate compound, having high refractivity and having both flexibility with which a lens formed therefrom is foldable and transparency capable of preventing (free of) the occurrence of the glistening, a process for the production of the above (meth)acrylate copolymer and a soft intraocular lens comprising the above (meth)acrylate copolymer.

substituted on the 1-position and 3-position of the phenyl group or on the 1-position and 4-position of the phenyl group.

$R_2$ in the general formula (I) includes, for example, a methylene group, an ethylene group, a propylene group, an isopropylene group, a butylene group, a hexylene group and an isohexylene group. The number of carbon atoms of $R_2$ is preferably 1 to 7, more preferably 1 to 6, still more preferably 1 to 3.

That Y is a single bond in the general formula (I) means that a group of $R_2$ and the phenyl group bond to each other directly.

Specific examples of the (meth)acrylate compound of the general formula (I) include the following compounds.

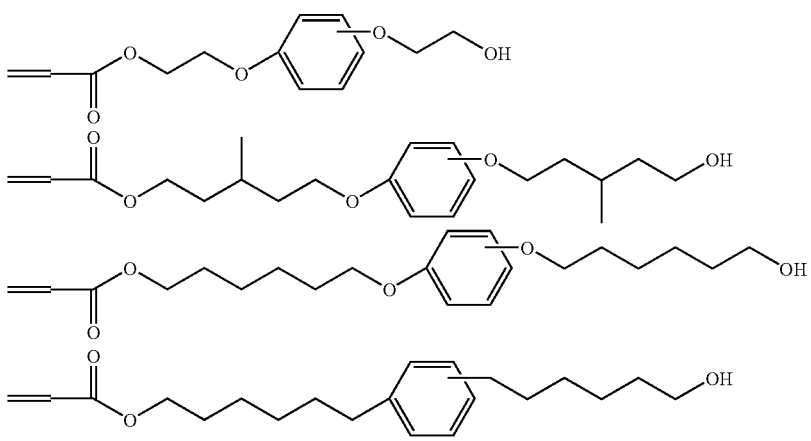

BEST MODES FOR PRACTICING THE INVENTION

[(Meth)Acrylate Compound and Process for the Production Thereof]

First, the (meth)acrylate compound of the present invention will be explained. It should be understood that "(meth)acrylate" as used in the present specification means both an acrylate and a methacrylate.

The (meth)acrylate compound of the present invention is represented by the general formula (I),

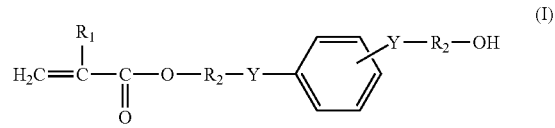

wherein $R_1$ is a hydrogen atom or methyl, $R_2$ is a linear or branched alkylene group having 1 to 8 carbon atoms and Y is a single bond or an oxygen atom.

The (meth)acrylate compound of the present invention, represented by the general formula (I), is not registered in CAS REG (Chemical Abstract Service Registry) and is a novel compound that is not described in any document.

In the general formula (I), the group of $CH_2=CR_1-CO-O-R_2-Y-$ and the group of $-Y-R_2-OH$ are preferably The process for the production of a (meth)acrylate compound, provided by the present invention, will be explained below.

The process for the production of a (meth)acrylate compound, provided by the present invention, comprises reacting a compound of the general formula (II),

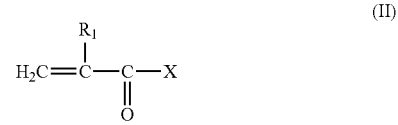

wherein $R_1$ is a hydrogen atom or methyl and X is a halogen atom, and a compound of the general formula (III),

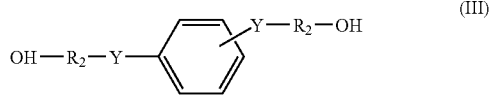

wherein $R_2$ is a linear or branched alkylene group having 1 to 8 carbon atoms and Y is a single bond or an oxygen atom.

In the general formula (II), X is a chlorine atom, bromine atom, or the like, and X is preferably a chlorine atom.

$R_2$ and Y in the general formula (III) have the same definitions as those of $R_2$ and Y in the above general formula (I).

In the process for the production of a (meth)acrylate compound, provided by the present invention, the reaction of the compound of the general formula (II) with the compound of the general formula (III) is preferably carried out in a solvent in the presence of a catalyst.

Concerning the amounts of the compound of the general formula (II) and the compound of the general formula (III) for use, their molar ratio (amount of the compound of the general formula (II)/amount of the compound of the general formula (III)) is preferably 45/55 to 5/95, more preferably 40/60 to 15/85.

The solvent can be preferably selected from cyclic ether solvents such as THF (tetrahydrofuran), dioxane and trioxane, while the solvent shall not be limited thereto.

The catalyst can be preferably selected from amine compounds such as triethylamine and diethylmethylamine and pyridine compounds such as 2,6-lutidine, while the catalyst shall not be limited thereto.

After completion of the reaction, a solution containing a reaction product is subjected to extraction, concentration, purification, etc., as required, whereby the intended (meth) acrylate compound can be obtained.

[(Meth)Acrylate Copolymer]

The (meth)acrylate copolymer of the present invention is characteristically a copolymer obtained by copolymerizing a monomer mixture containing a (meth)acrylate monomer (A) of the general formula (I),

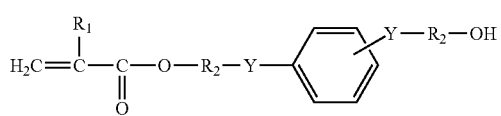

wherein $R_1$ is a hydrogen atom or methyl, $R_2$ is a linear or branched alkylene group having 1 to 8 carbon atoms and Y is a single bond or an oxygen atom, a monomer (B) copolymerizable with the (meth)acrylate monomer (A) and a crosslinking monomer (C).

As a (meth)acrylate monomer (A), one or two or more (meth)acrylate compounds selected from the above (meth) acrylate compounds of the present invention can be used, and specific examples thereof are also those which are already described as specific examples of the (meth)acrylate compound of the present invention.

Since the (meth)acrylate copolymer of the present invention contains a unit derived from the (meth)acrylate monomer (A) as a structural unit, the refractive index of a copolymer to be obtained can be improved, and when the (meth)acrylate copolymer is processed in the form of an intraocular lens, the phenomenon that impairs the transparency of the lens, such as the glistening phenomenon, can be inhibited.

The monomer (B) includes one or two or more monomers copolymerizable with the monomer (A), and examples thereof include various (meth)acrylate monomers (excluding the monomer (A)). In particular, it is preferred to use a monomer ($B_1$) of the general formula (IV),

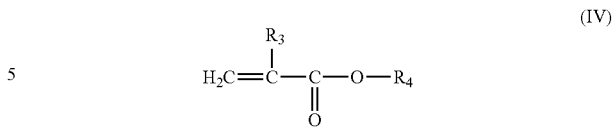

wherein $R_3$ is a hydrogen atom or methyl and $R_4$ is a linear or branched alkyl group having 3 to 12 carbon atoms, and/or a monomer ($B_2$) of the general formula (V),

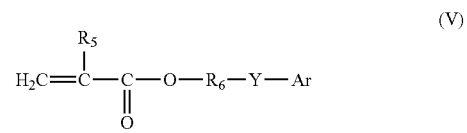

wherein $R_5$ is a hydrogen atom or methyl, $R_6$ is a single bond or a linear or branched alkylene group having 1 to 8 carbon atoms, Y is a single bond or an oxygen atom and Ar is a substituted or non-substituted phenyl group or 4-(α,α-dimethylbenzyl)phenyl.

When the monomer ($B_1$) and/or the monomer ($B_2$) are/is used as the monomer (B), there can be obtained a copolymer imparted with flexibility, and when the copolymer is processed in the form of an intraocular lens, the intraocular lens is easily foldable.

The number of carbon atoms of $R_4$ in the general formula (IV) is preferably 3 to 10, more preferably 3 to 8.

Specific examples of the monomer ($B_1$) of the general formula (IV) include n-butyl(meth)acrylate, isobutyl(meth) acrylate, isoamyl(meth)acrylate, hexyl (meth)acrylate, 2-ethylhexyl(meth)acrylate, n-octyl (meth)acrylate, isooctyl (meth)acrylate, decyl (meth)acrylate and isodecyl(meth) acrylate.

The number of carbon atoms of $R_6$ in the general formula (V) is preferably 1 to 7, more preferably 1 to 6, still more preferably 1 to 3.

That Y is a single bond in the general formula (V) means that a group of $R_6$ and a group of Ar bond to each other directly.

Specific examples of the monomer ($B_2$) of the general formula (V) include 2-phenylethyl(meth)acrylate, 2-ethylphenoxy(meth)acrylate, phenyl(meth)acrylate, benzyl (meth)acrylate, 3-phenylpropyl(meth)acrylate, 4-phenylbutyl(meth)acrylate and 4-(α,α-dimethylbenzyl)phenoxyethyl (meth)acrylate.

In addition to the above monomers, the monomer (B) includes fluorine-containing (meth)acrylates such as perfluorooctylethyloxypropylene methacrylate and trifluoroethyl methacrylate.

In the (meth)acrylate copolymer of the present invention, the mass ratio of the unit from the monomer (A) and the unit derived from the monomer (B) (mass of the unit from the monomer (A)/mass of the unit derived from the monomer (B)) is preferably 1/99 to 40/60, more preferably 5/95 to 30/70.

That is, the amount of the unit from the monomer (A) contained in the copolymer is preferably 1 to 40 mass %, more preferably 5 to 30 mass % based on the total amount of the unit derived from the monomer (A) and the unit derived from the monomer (B). When the above amount of the unit derived from the monomer A is less than 1 mass %, it is difficult to produce an effect that a decrease in transparency (so-called glistening and the like) is inhibited. When it exceeds 40 mass %, undesirably, the compatibility of the monomers to each other comes to be poor.

Further, the amount of the unit derived from the monomer (B) contained in the copolymer is preferably 60 to 99 mass %, more preferably 70 to 95 mass % based on the total amount of the unit derived from the monomer (A) and the unit derived from the monomer (B). When the amount of the unit derived from the monomer (B) is less than 60 mass %, the compatibility of the monomers to each other comes to be poor. When it exceeds 99 mass %, it is difficult to produce an effect that a decrease in transparency (so-called glistening and the like) is inhibited.

The crosslinking monomer (C) refers to one or two or more monomers that can bond to one or both of the monomer (A) and the monomer (B).

When the crosslinking monomer (C) is used, the plastic deformation of a lens can be prevented and the lens can be further improved in mechanical strength when an obtained copolymer is processed in the form of a lens.

Examples of the crosslinking monomer (C) include 1,9-nonanediol di(meth)acrylate, ethylene glycol di(meth)acrylate, 2-hydroxy-1,3-di(meth)acryloxypropane, diethylene glycol di(meth)acrylate, triethylene glycol di(meth)acrylate, tetraethylene glycol di(meth)acrylate, 1,4-butanediol di(meth)acrylate and 1,6-hexanediol di(meth)acrylate.

The content of a unit derived from the crosslinking monomer (C) is preferably 0.5 to 6 mass %, more preferably 1 to 5 mass % based on the total amount (100 mass %) of the unit derived from the monomer (A) and the unit derived from the monomer (B). When the above content is less than 0.5 mass %, the effect produced by the introduction of the crosslinking monomer is not easily exhibited. When it exceeds 6 mass %, undesirably, the copolymer is fragile since the number of crosslinking points increases, and the mechanical strength of the copolymer is liable to be decreased.

In addition to the units derived from the above monomers (A) to (C), the (meth)acrylate copolymer of the present invention can contain, as a structural unit, one or two or more units derived from monomers having capability of absorbing ultraviolet ray.

The content of the unit(s) derived from monomers having capability of absorbing ultraviolet ray, is preferably 0.05 to 3 mass %, more preferably 1 to 2 mass % based on the total amount (100 mass %) of the unit derived from the monomer (A) and the unit derived from the monomer (B). When the above content is less than 0.05 mass %, no effect on the prevention of ultraviolet ray can be expected. When it exceeds 3 mass %, no further remarkable effect on the prevention of ultraviolet ray can be expected.

As a monomer having capability of absorbing ultraviolet, any monomer can be used so long as it has capability of absorbing ultraviolet ray and can react with one or both of the monomer (A) and the monomer (B). In particular, a compound of the following formula (VI) (2-(2'-hydroxy-3'tert-butyl-5'-methylphenyl)-5-(2'-methacryloxyethyl)benzotriazole) can be used.

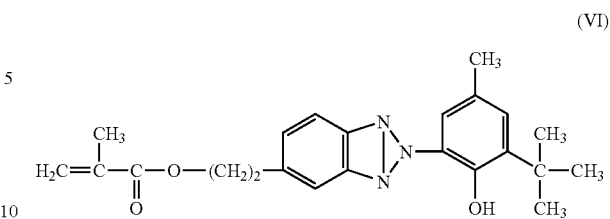

Further, the (meth)acrylate copolymer of the present invention can contain, as a structural unit, one or two or more units derived from monomers having capability of coloring the (meth)acrylate copolymer in yellow.

The content of the unit derived from the monomer(s) having capability of coloring the (meth)acrylate copolymer in yellow is preferably 0.005 to 0.5 mass %, more preferably 0.01 to 0.2 mass % based on the total amount (100 mass %) of the unit derived from the monomer (A) and the unit derived from the monomer (B).

As a monomer having capability of coloring the (meth)acrylate copolymer in yellow, any monomer can be used so long as it has capability of coloring the (meth)acrylate copolymer in yellow and can react with one or both of the monomer (A) and the monomer (B). In particular, a compound of the following formula (VII) (4-(5-hydroxy-3-methyl-1-phenyl-4-pyrzolylmethylene)-3-methacrylamino-1-phenyl-2-pyrazolin-5-one) can be used.

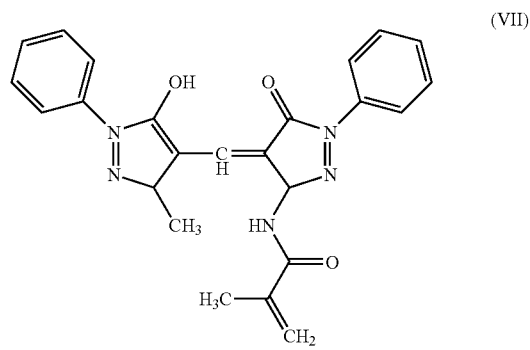

In addition, the (meth)acrylate copolymer of the present invention may further contain, as a structural unit, a unit derived from a reactive monomer having the property of being photochromic.

The (meth)acrylate copolymer of the present invention preferably has properties that a soft intraocular lens, to which it is the most preferably applied, is required to have. For example, preferably, the (meth)acrylate copolymer is colorless and transparent in appearance and has a refractive index of 1.50 to 1.59, a tensile strength of 60 to 2,000 g and a folding load of 15 to 2,000 g. The above values of the refractive index, tensile strength and folding load refer to values measured by methods described in Examples to be described later.

The (meth)acrylate copolymer of the present invention includes a block copolymer and a random copolymer, while it is generally a random copolymer.

[Process for the Production of (Meth)Acrylate Copolymer]

The process for the production of a (meth)acrylate copolymer, provided by the present invention, will be explained below.

The process for the production of a (meth)acrylate copolymer, provided by the present invention, comprises copolymerizing a monomer mixture containing a monomer (A) of the general formula (I),

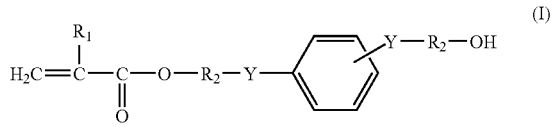

wherein $R_1$ is a hydrogen atom or methyl, $R_2$ is a linear or branched alkylene group having 1 to 8 carbon atoms and Y is a single bond or an oxygen atom, a monomer (B) copolymerizable with the monomer (A) and a crosslinking monomer (C), in the presence of a polymerization catalyst and/or under a condition where light is applied.

In the process for the production of a (meth)acrylate copolymer, provided by the present invention, the monomers (A) to (C) as raw materials include those which are explained with regard to the above (meth)acrylate copolymer of the present invention. Further, there can be also used those monomers which are explained as monomers other than the monomers (A) to (C) with regard to the above (meth)acrylate copolymer of the present invention.

As a method for producing the copolymer, for example, there can be employed a thermal polymerization method in which a radical polymerization initiator or photopolymerization initiator is added to a mixture of the above monomers as materials, the mixture is fully stirred to prepare a homogeneous monomer mixture and the monomer mixture is temperature-increased stepwise or continuously in the temperature range of 40 to 120° C. or a photopolymerization method in which ultraviolet light or visible light is applied to the monomer mixture.

Specific examples of the above radical polymerization initiator include azo initiators such as 2,2-azobis(4-methoxy-2,4-dimethylvaleronitrile), 2,2-azobis(2,4-dimethylvaleronitrile), 2,2-azobis(2-methylpropionitrile) and 2,2-azobis(2-methylbutyronitrile) which are generally known as radical polymerization initiators and organic peroxides such as bis(4-t-butylcyclohexyl)peroxydicarbonate, benzoyl peroxide, 1,1,3,3-tetramethylbutyl hydroperoxide, t-hexyl hydroperoxide, t-butyl hydroperoxide and 3,5,5-trimethylhexanol peroxide.

Specific examples of the photopolymerization initiator include methyl o-benzoyl benzoate, 1-hydroxy-cyclohexyl-phenyl-ketone, 2-hydroxy-2-methoxy-1-phenylpropan-1-one, 1-[4-(2-hydroxyethoxy)-phenyl]-2-hydroxy-2-methyl-1-propan-1-one and bis(2,4,6-trimethylbenzoyl)-phenylphosphine oxide.

The polymerization initiators may be used singly or as a mixture including two or more of them. The amount of the polymerization initiator is preferably approximately 0.05 to 5 mass % based on the total monomer amount.

In the thermal polymerization method, the reaction time period is preferably 1 hour to 80 hours, more preferably 2 hours to 48 hours. In the photopolymerization method, the reaction time period is preferably 1 minute to 3 hours, more preferably 2 minutes to 2 hours.

The resultant reaction mixture is subjected to extraction procedures such as supercritical extraction or solvent extraction using a good solvent such as acetone, methyl ethyl ketone or the like, and the amount of an unreacted monomer extracted is measured with a gas chromatograph mass analyzer or the like, whereby it can be ascertained whether or not the polymerization is completed.

When the polymerization is carried out in a proper mold or vessel, a copolymer having the form, for example, of a rod, a block or a plate can be obtained. A molded product formed of a desired copolymer can be also obtained by a method in which a mixture of monomers as raw materials is charged into a mold having a form corresponding to the form of a molded article as an end product, then a pressure is applied and the polymerization and the molding are carried out in one mold (this method will be referred to as "mold method" hereinafter). When the polymerization and the molding are carried out by the mold method, the pressure that is exerted on the copolymer is preferably 1 to 5 kgf/cm².

[Soft Intraocular Lens]

The intraocular lens of the present invention comprises the above (meth)acrylate copolymer of the present invention.

The intraocular lens is generally constituted of an optic portion (lens portion) and support portions (haptic portions). The intraocular lens of the present invention has an optic portion that is at least required to be formed of the (meth)acrylate copolymer of the present invention, and the haptic portions thereof may be formed, for example, of polypropylene, PMMA (polymethyl methacrylate), polyimide or the like.

Further, the surface of the optic portion may be surface-treated by plasma treatment using argon, oxygen or nitrogen gas.

The soft intraocular lens of the present invention can be produced by obtaining a copolymer in the form of a rod, a block or a plate and then cutting and polishing the copolymer at a low temperature or by the above mold method using a mold having a form corresponding to the form of an intended lens.

Further, there may be employed a constitution in which the haptic portions and the optic portion are separately prepared and the haptic portions are fixed to the optic portion to produce the intraocular lens or a constitution in which the optic portion and the haptic portions are integrally produced.

EXAMPLES

The present invention will be explained more in detail with reference to Examples hereinafter, while the present invention shall not be limited by these Examples.

Example 1

Preparation Example of (Meth)Acrylate Compound

A 500 ml flask was charged with 13.9 g (70 mmol) of 1,4-bis(2-hydroxyethoxy)benzene, 280 ml of THF (tetrahydrofuran), 7.1 g (70 mmol) of triethylamine and a very small amount of phenothiazine, followed by stirring under the current of argon.

After the above-stirred solution was cooled to approximately 20° C., and a solution of 4.2 g (35 mmol) of acryloyl chloride in THF was dropwise added to carry out a reaction at room temperature. After the reaction was carried out for 1 hour, ice water and ethyl acetate were added to carry out extraction. A separated organic layer was washed with brine (salt water) and dried over anhydrous sodium sulfate ($Na_2SO_4$), followed by filtering. The resultant filtrate was concentrated and then purified with a column to give 3.2 g of a white crystal. Further, the white crystal was recrystallized to give 2.4 g (yield: 27%) of a white crystal (melting point: 55°

C.). As a result of H-NMR analysis, it was ascertained that the thus-obtained white crystal was 1,4-bis(2-hydroxyethoxy) phenyl acrylate having the following structural formula (to be referred to as "HEPA" hereinafter).

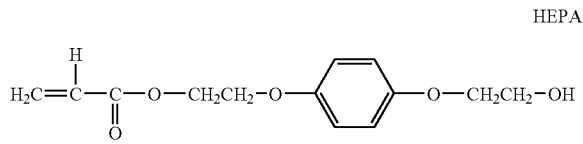

HEPA

Example 2

Process for Producing (Meth)Acrylate Copolymer and Soft Intraocular Lens

A sample tube having a volume of 30 ml was charged with 10 mass % of HEPA prepared in the above Example 1 as a monomer (A), 40 mass % of butyl acrylate ("BA" hereinafter) as a monomer ($B_1$), 50 mass % of 2-phenylethyl methacrylate ("PEMA" hereinafter) as a monomer ($B_2$), 5 mass %, based on the total amount of HEPA, BA and PEMA, of ethylene glycol dimethacrylate ("EDMA" hereinafter) as a crosslinking monomer (C), and 0.4 mass %, based on the total amount of HEPA, BA and PEMA, of azoisobutyronitrile (AIBN) as a polymerization initiator as shown in Table 1 to be described later, and these materials were fully stirred to give a homogeneous monomer mixture solution.

The above solution was cast into an intraocular-lens-producing mold formed of polypropylene and temperature-increased up to a temperature of 100° C. in a pressure polymerization furnace in a nitrogen atmosphere of a pressure of 2.5 kgf/cm², and then polymerization was carried out for 2 hours to give a copolymer (diameter 6 mm, thickness 0.6 mm) having the form of an optic portion of an intraocular lens.

Separately, the same monomer mixture solution as the above was polymerized in a box-shaped vessel to give a copolymer having the form of a sheet (15 mm long, 15 mm wide and 0.6 mm thick).

The thus-obtained copolymer was immersed in 100 ml of methanol to remove unreacted monomers and fully dried, and the copolymer was measured for various physical properties by the following methods. Table 2 shows the results.

1. Appearance

A copolymer (diameter 6 mm, thickness 0.6 mm) having the form of an optic portion of an intraocular lens was immersed in water at 23° C. for 24 hours, and then, light from an LG-PS2 white light lamp supplied by Olympus Optical Co., Ltd. was applied to the side surface of the copolymer. And, the copolymer was visually observed to evaluate it for whether or not it had a change in transparency and color. The evaluation was conducted on the following ratings.

[Evaluation Ratings]
○: Colorless and transparent
Δ: Slightly opacified
X: Opacified 2. Tensile Strength An obtained copolymer having the form of a sheet was processed so as to have a dumbbell-shaped form (total length 10 mm, width of the narrowest portion 1 mm, thickness 0.6 mm), and the thus-prepared sample was tensioned with a universal material-testing machine 4301-H0776 supplied by Instron Japan Co., Ltd. to measure the copolymer for a tensile strength. The copolymer was tensioned at a tension rate of 100 mm/minute (the unit of data is g).

3. Folding Load

A copolymer (diameter 6 mm, thickness 0.6 mm) having the form of an optic portion of an intraocular lens was fixed with holding tools and folded with a universal material-testing machine 4301-H0776 supplied by Instron Japan Co., Ltd. to measure a folding load. The measurement was conducted at a folding speed of 100 mm/minute at a folding distance of 3.6 mm (the unit of data is g).

4. Refractive Index

With a refractometer DR-M2 supplied by ATAGO CO., LTD., a copolymer (diameter 6 mm, thickness 0.6 mm) having the form of an optic portion of an intraocular lens was measured at 23° C. using e-ray (546.1 nm).

5. Glistening

A copolymer (diameter 6 mm, thickness 0.6 mm) having the form of an optic portion of an intraocular lens was immersed in water at 33° C. for 24 hours and then immersed in water at 28° C. or 23° C., and the appearance of the copolymer was observed through a stereoscopic microscope (U-PMTVC, supplied by Olympus Optical Co., Ltd.) to evaluate it on the basis of the following ratings.

(Evaluation Ratings)

A: Even in a temperature change from 33° C. to 23° C. in water, no glistening occurs and excellent transparency is maintained.

B: In a temperature change from 33° C. to 23° C. in water, slight glistening is observed, but in a temperature change from 33° C. to 28° C. in water, no glistening occurs and excellent transparency is maintained.

C: In a temperature change from 33° C. to 23° C. in water, intense glistening occurs, and in a temperature change from 33° C. to 28° C. in water, slight glistening is observed.

D: Even in a temperature change from 33° C. to 28° C. in water, intense glistening occurs.

E: Glistening exists in a material from the beginning regardless of a change in temperature, and the material is non-transparent.

It is seen from Table 2 that the copolymer obtained in Example 2 has no problem on its appearance in water and exhibits a proper tensile strength and a small folding load (easily foldable), and that it has properties suitable for a soft intraocular lens. It is further seen that the copolymer obtained in Example 2 has a refractive index of 1.522 and is free from a transparency-impairing phenomenon such as so-called glistening in a temperature change in water.

Examples 3-12 and Comparative Examples 1-6

Copolymers each having the form of an optic portion of an intraocular lens were obtained in the same manner as in Example 2 except that the monomers as raw materials and the amounts thereof were changed as shown in Table 1, and they were evaluated for various properties in the same manner as in Example 2. Table 2 shows the results.

In addition, each of the copolymers obtained in Examples 2 to 12 was subjected to Soxhlet extraction with a good solvent such as acetone, methyl ethyl ketone or the like for 6 hours, and total amounts of unreacted monomers were measured with a gas chromatograph mass analyzer to show 50 ppm or less in all the Examples.

Abbreviations in Table 1 correspond to substance names as follows.

HEPA: 1,4-Bis(2-hydroxyethoxy)phenyl acrylate
BA: Butyl acrylate
BRM: Perfluorooctylethyloxypropylene methacrylate
PEA: 2-Phenylethyl acrylate
PEMA: 2-Phenylethyl methacrylate
POEMA: 2-Phenoxyethyl methacrylate
HPPA: 2-Hydroxy-3-phenoxypropyl acrylate
TFEMA: Trifluoroethyl methacrylate
NODN: 1,9-Nonanediol dimethacrylate
EDMA: Ethylene glycol dimethacrylate
GAMA: 2-Hydroxy-1-acryloxy-3-methacryloxypropane
AIBN: Azobisisobutyronitrile
V-65: 2,2'-Azobis(2,4-dimethylvaleronitrile)
T-150: 2-(2'-Hydroxy-3'tert-butyl-5'-methylphenyl)-5-(2'-methacryloxyethyl)benzotriazole
HMPO: 4-(5-Hydroxy-3-methyl-1-phenyl-4-pyrazolylmethylene)-3-methacrylamino-1-phenyl-4-pyrazolin-5-one

TABLE 1

| | Monomer (A) | Monomer (B) | | | | | | | Crosslinking monomer (C) | | | Polymerization initiator | | UV M'mer *1 | Yellow. M'mer *2 |
|---|---|---|---|---|---|---|---|---|---|---|---|---|---|---|---|
| | | Monomer (B$_1$) | Monomer (B$_2$) | | | | | | | | | | | | |
| | HEPA | HPPA | BA | PEA | PEMA | POEMA | BRM | TFEMA | NODN | EDMA | GAMA | AIBN | V-65 | T-150 | HMPO |
| Ex. 2 | 10 | | 40 | | 50 | | | | | 5 | | 0.4 | | | |
| Ex. 3 | 10 | | 32 | | 50 | | 8 | | | 5 | | 0.4 | | | |
| Ex. 4 | 10 | | 32 | | 50 | | 8 | | | 3 | | 0.4 | | | |
| Ex. 5 | 10 | | | 90 | | | | | | 5 | | 0.4 | | | |
| Ex. 6 | 10 | | 32 | | 50 | | 8 | | 5 | | | 0.4 | | | |
| Ex. 7 | 10 | | 32 | | 50 | | 8 | | | 5 | | 0.4 | | 1.5 | |
| Ex. 8 | 10 | | 32 | | 50 | | 8 | | | 5 | | 0.4 | | 1.5 | |
| Ex. 9 | 5 | | 32 | | 55 | | 8 | | | 5 | | 0.4 | | 1.5 | 0.03 |
| Ex. 10 | 25 | | 75 | | | | | | | 5 | | 0.4 | | | |
| Ex. 11 | 18 | | 77 | | | | | 5 | | 5 | | 0.4 | | 1.5 | |
| Ex. 12 | 18 | | 77 | | | | | 5 | | 5 | | 0.4 | | 1.5 | 0.02 |
| CEx. 1 | | | 100 | | | | | | 5 | | | 0.4 | | | |
| CEx. 2 | | 100 | | | | | | | | | | | 1 | 0.2 | | |
| CEx. 3 | | 100 | | | | | | | | | | 5 | | 0.2 | | |
| CEx. 4 | | 50 | | | 50 | | | | | | | | 1 | 0.2 | | |
| CEx. 5 | | 50 | | | 50 | | | | | | | 5 | | 0.2 | | |
| CEx. 6 | | 10 | 40 | | 50 | | | | | | 5 | | 5 | 0.2 | | |

*1 = Monomer having ultraviolet absorption capability
*2 = Monomer having yellow coloring capability
Ex. = Example,
CEx. = Comparative Example

TABLE 2

| | Appearance | Tensile strength | Folding load | Refractive index | Glistening |
|---|---|---|---|---|---|
| Ex. 2 | ○ | 427 | 165 | 1.522 | A |
| Ex. 3 | ○ | 402 | 178 | 1.515 | A |
| Ex. 4 | ○ | 253 | 122 | 1.512 | B |
| Ex. 5 | ○ | 94 | 83 | 1.555 | B |
| Ex. 6 | ○ | 377 | 111 | 1.511 | B |
| Ex. 7 | ○ | 413 | 171 | 1.518 | B |
| Ex. 8 | ○ | 407 | 167 | 1.524 | B |
| Ex. 9 | ○ | 474 | 186 | 1.526 | B |
| Ex. 10 | ○ | 91 | 31 | 1.540 | A |
| Ex. 11 | ○ | 110 | 38 | 1.554 | B |
| Ex. 12 | ○ | 106 | 37 | 1.554 | B |
| CEx. 1 | ○ | 85 | 33 | 1.559 | D |
| CEx. 2 | X | 500 or more | 2200 or more | 1.554 | E |
| CEx. 3 | X | 500 or more | 2200 or more | 1.559 | D |
| CEx. 4 | X | 500 or more | 2200 or more | 1.562 | E |
| CEx. 5 | Δ | 500 or more | 2200 or more | 1.568 | D |
| CEx. 6 | ○ | 467 | 869 | 1.533 | D |

Ex. = Example,
CEx. = Comparative Example

It is seen from Table 2 that the copolymers obtained in Examples 3 to 12 similarly have no problem on its appearance in water and exhibit proper tensile strengths and small folding loads, and that they have properties suitable for a soft intraocular lens. It is further seen that these copolymers have refractive indices of more than 1.5 and have a high effect on inhibition of a transparency-impairing phenomenon such as so-called glistening in a temperature change in water.

On the other hand, the copolymer obtained in Comparative Example 1 has no problem on its appearance in water and exhibit a proper tensile strength and a small folding load as shown in Table 2. However, it is seen that glistening occurs in the copolymer due to a change in temperature in water since the copolymer contains no unit derived from HEPA.

As shown in Table 1, further, the copolymers obtained in Comparative Examples 2 to 6 contain units derived from HPPA in place of the unit derived from HEPA and further contain units derived GAMA as a crosslinking monomer, and they all have proper tensile strengths and refractive indices as shown in Table 2. However, the copolymers of Comparative Examples 2 to 5 are opacified when they are only stored in water having room temperature for 24 hours, and they show large folding loads, and it is seen that they are not suitable for any soft intraocular lens. Further, it is seen that the copolymers of Comparative Examples 3, 5 and 6 heavily suffer the occurrence of glistening even in a temperature change from 33° C. to 28° C., and that the copolymers of Comparative Examples 2 and 4 have glistening in their materials from the beginning and are non-transparent regardless of a change in temperature.

INDUSTRIAL UTILITY

According to the present invention, there can be provided novel (meth)acrylate compound and a process for the production thereof, a (meth)acrylate copolymer having a unit derived from the above (meth)acrylate compound, having high refractivity and having both flexibility with which a lens formed therefrom is foldable and transparency capable of preventing (free of) the occurrence of the glistening, a process for the production of the above (meth)acrylate copolymer and a soft intraocular lens comprising the above (meth)acrylate copolymer.

The invention claimed is:

1. A soft intraocular lens comprising a (meth)acrylate copolymer obtained by copolymerization of a monomer mixture containing a methacrylate monomer (A) of the general formula (I),

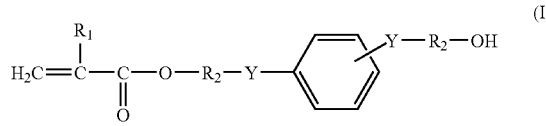

(I)

wherein $R_1$ is a hydrogen atom or methyl, $R_2$ is a linear or branched alkylene group having 1 to 8 carbon atoms and Y is a single bond or an oxygen atom,
a monomer (B) copolymerizable with the (meth)acrylate monomer (A) and a crosslinking monomer (C).

2. The soft intraocular lens of claim 1, wherein a unit derived from the monomer (A) and a unit derived from the monomer (B) have a mass ratio (a mass of the unit derived from the monomer (A)/a mass of the unit derived from the monomer (B)) of 1/99 to 40/60.

3. The soft intraocular lens of claim 1, wherein the monomer (B) is selected from a monomer ($B_1$) of the general formula (IV),

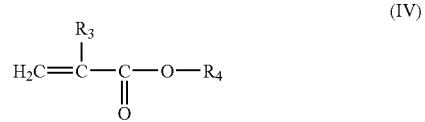

(IV)

wherein $R_3$ is a hydrogen atom or methyl and $R_4$ is a linear or branched alkyl group having 3 to 12 carbon atoms, or a monomer ($B_2$) of the general formula (V),

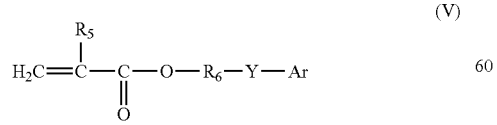

(V)

wherein $R_5$ is a hydrogen atom or methyl, $R_6$ is a single bond or a linear or branched alkylene group having 1 to 8 carbon atoms, Y is a single bond or an oxygen atom and Ar is a substituted or non-substituted phenyl group or 4-(α,α-dimethylbenzyl)phenyl.

4. The soft intraocular lens of claim 1, which contains a unit derived from a monomer having capability of absorbing ultraviolet ray.

5. The soft intraocular lens of claim 4, which contains 0.05 to 3 mass %, based on the total amount of a unit derived from the monomer (A) and a unit derived from the monomer (B), of a unit derived from the monomer having capability of absorbing ultraviolet ray.

6. The soft intraocular lens of claim 4, herein the monomer having capability of absorbing ultraviolet is a compound of the formula (VI).

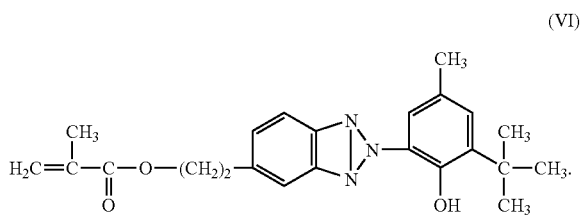

(VI)

7. The soft intraocular lens of claim 1, which contains a unit derived from a monomer having capability of coloring the (meth)acrylate copolymer in yellow.

8. The soft intraocular lens of claim 7, which contains 0.005 to 0.5 mass %, based on the total amount of a unit derived from the monomer (A) and a unit from the monomer (B), of the unit derived from a monomer having capability of coloring the (meth)acrylate copolymer in yellow.

9. The soft intraocular lens of claim 7, wherein the monomer having capability of coloring the (meth)acrylate copolymer in yellow is a compound of the formula (VII).

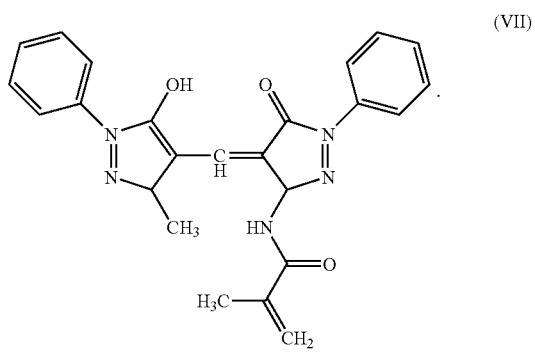

(VII)

* * * * *